(12) United States Patent
Berg et al.

(10) Patent No.: US 6,583,879 B1
(45) Date of Patent: Jun. 24, 2003

(54) BENCHTOP SPECTROPHOTOMETER WITH IMPROVED TARGETING

(75) Inventors: Bernard J. Berg, Kentwood, MI (US); Frederick J. Maddage, Jr., Danbury, NH (US); Richard Maurice Montminy, Newbury, NH (US); Kevin Tougas, Sunapee, NH (US)

(73) Assignee: X-Rite, Incorporated, Grandville, MI (US)

( * ) Notice: Subject to any disclaimer, the term of this patent is extended or adjusted under 35 U.S.C. 154(b) by 0 days.

(21) Appl. No.: 10/044,529

(22) Filed: Jan. 11, 2002

(51) Int. Cl.[7] .................................................. G01J 3/50
(52) U.S. Cl. ........................ 356/402; 356/236; 250/226; 250/228
(58) Field of Search ................................ 356/402, 236; 250/226, 228

(56) References Cited

U.S. PATENT DOCUMENTS

| | | | |
|---|---|---|---|
| 3,986,778 A | 10/1976 | Mathisen et al. | |
| 4,101,222 A | 7/1978 | Mathisen | |
| 4,757,550 A | 7/1988 | Uga | |
| 5,369,481 A | 11/1994 | Berg et al. | |
| 5,408,294 A | 4/1995 | Lam | |
| 5,633,676 A | 5/1997 | Harley et al. | |
| 5,636,015 A | 6/1997 | Imura et al. | |
| 5,706,083 A | * 1/1998 | Iida et al. | 356/328 |
| 5,946,131 A | 8/1999 | Wells et al. | |
| 6,008,905 A | 12/1999 | Breton et al. | |
| 6,011,648 A | 1/2000 | Mukai et al. | |
| 6,020,959 A | 2/2000 | Imura | |
| 6,038,024 A | 3/2000 | Berner | |
| 6,061,140 A | 5/2000 | Berg et al. | |
| 6,275,295 B1 | * 8/2001 | Sopori | 356/446 |

FOREIGN PATENT DOCUMENTS

JP  0098176  9/1998

OTHER PUBLICATIONS

P.A. Palumbo, Novel spectrophotometer for the measurement of color and appearance, *Analytica Chimica Acta*, 380 (1999) pp. 243–261.

* cited by examiner

*Primary Examiner*—F. L. Evans
(74) *Attorney, Agent, or Firm*—Warner Norcross & Judd LLP

(57) ABSTRACT

A color measurement instrument with improved sample targeting or positioning. The system includes an integrating sphere, a beam splitter, a video camera, and a spectrograph. The beam splitter is aligned with the viewing port of the spectrophotometer to deliver the light reflected from the sample to both the video camera and the spectrograph. The video camera provides an image of the position of the sample with respect to the viewing port of the sphere, enabling the visual observation and evaluation of the sample position prior to use of the spectrophotometer.

20 Claims, 6 Drawing Sheets

BENCHTOP SPECTROPHOTOMETER WITH IMPROVED TARGETING

BACKGROUND OF THE INVENTION

The present invention relates to spectrophotometers, and more particularly to benchtop spectrophotometers.

Spectrophotometers are instruments used to determine the color of a sample. A spectrophotometer typically includes a source of illumination to illuminate the sample, a color measurement engine for detecting light reflected from the sample, and signal processing circuitry connected to the light measurement engine to compute curves or numerical values indicative of the color of the sample. The general principles of construction and use of spectrophotometers are well known to those skilled in the color measurement art.

One type of spectrophotometer uses an integrating sphere in which the light illuminating the sample is integrated to provide diffuse, uniform illumination over an exposed measurement area of the sample. Examples of such spectrophotometers are illustrated in U.S. Pat. No. 6,061,140 issued May 9, 2000, entitled "Spectrophotometer With Selectable Measurement Area"; and U.S. Pat. No. 5,369,481, issued Nov. 29, 1994, entitled "Portable Spectrophotometer." Both disclosed spectrophotometers are "portable" or "hand-held" units, in which the instrument is placed against the sample.

Other spectrophotometers are "benchtop" units providing ultra-high levels of precision in determining color. As the name implies, benchtop units are stationary, and the samples to be measured are placed in or on the units for analysis. A significant challenge with benchtop units is the accurate positioning of the sample within the sample port, so that the desired area of the sample is measured. Accurate positioning of the sample is critical to accurate measurement.

Prior artisans have taken two approaches in providing visual evaluation of the position of a sample within the sample port of a spectrophotometer. One instrument includes an optical port aligned with the sample port. A user may look through the port to visually observe the position of the sample within the sample port. However, use of the optical port can be physically awkward as the operator positions her eye and head to look into the sphere interior. Another instrument includes a split integrating sphere that can be opened to permit direct observation of the sample within the sample port. This procedure is awkward and exposes the sphere interior to possible dirt, smudges, and physical damage.

SUMMARY OF THE INVENTION

The aforementioned problems are overcome in the present invention in which a video camera is used to monitor the position of the sample within the sample port prior to color measurement.

As disclosed, the system includes an integrating sphere, a beam splitter, a video camera, and a color measurement system. The beam splitter is aligned with the viewing port of the sphere so that light reflected from the sample is directed both to the video camera and to the color measurement system. The image acquired by the video camera can be observed to evaluate position of the sample within the sample port. If the position is not as desired, the sample is manually repositioned and rechecked until it is as desired. After the sample position is confirmed as accurate, the color measurement is taken.

Accordingly, the present invention permits the visual, real-time confirmation of proper sample position with respect to a color measurement before the color measurement is taken.

These and other objects, advantages, and features of the invention will be more readily understood and appreciated by reference to the detailed description of the preferred embodiment and the drawings.

DETAILED DESCRIPTION OF THE PREFERRED EMBODIMENT

I. Overview

Figure 3:
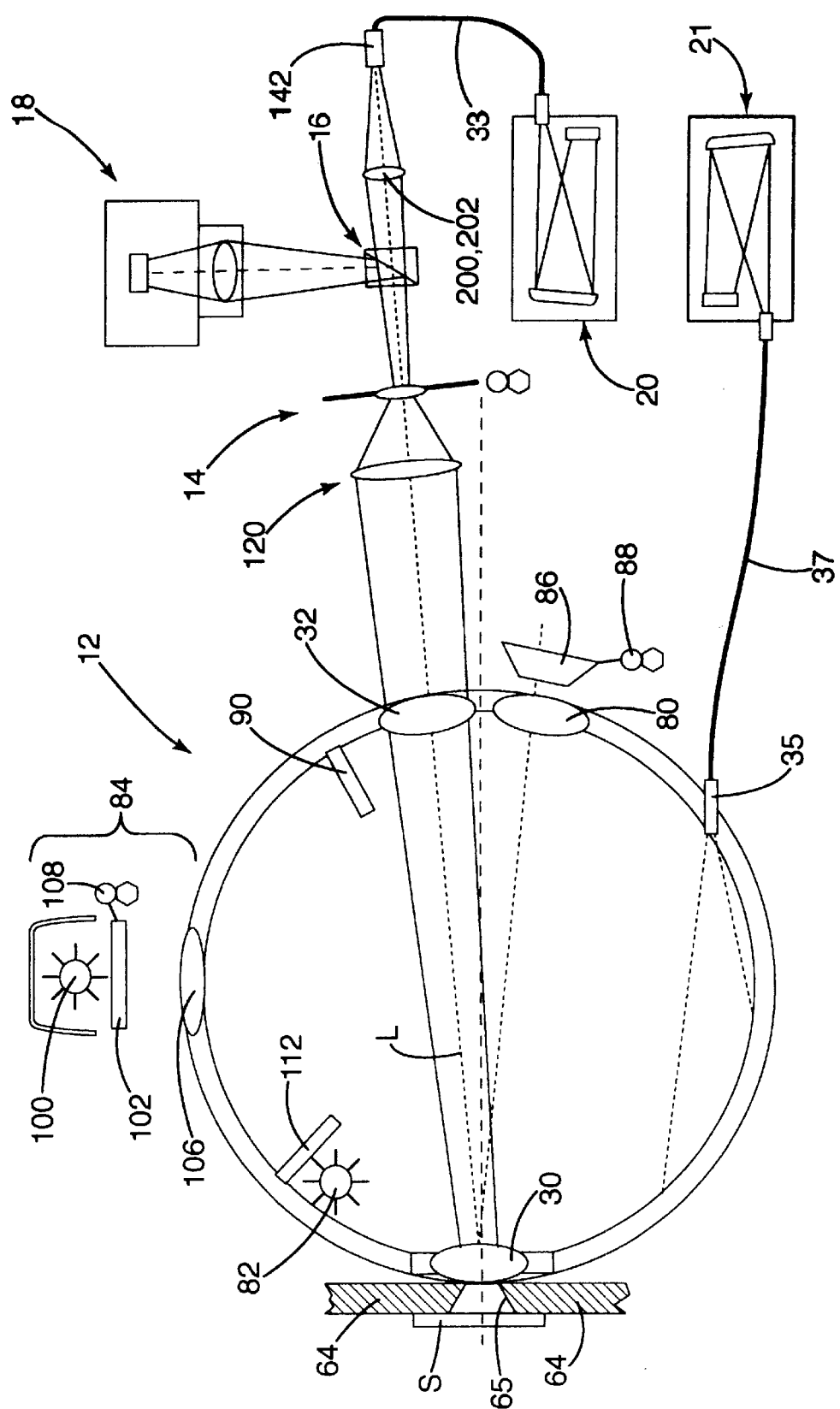
FIG. 3 is a schematic diagram of the major components of the spectrophotometer.

A benchtop spectrophotometer constructed in accordance with a preferred embodiment of the invention is illustrated in the drawings and generally designated 10. The major components of the spectrophotometer are schematically illustrated in FIG. 3 and include an integrating sphere 12, a reticule/aperture wheel 14, a beam splitter 16, a video camera 18, a sample spectrograph 20, and a reference spectrograph 21. The sphere includes a sample port 30 and a viewing port 32. The reticule/aperture wheel 14 and the beam splitter 16 are optically aligned with both the viewing port 32 and the sample port 30 so that light reflected from the sample passes through the beam splitter. The video camera 18 and the sample spectrograph 20 are optically aligned—physically in the case of the camera and by way of the fiber optic cable 33 in the case of the sample spectrograph—so that both the camera and the sample spectrograph receives the identical information.

In use as schematically illustrated in FIG. 3, a sample S is placed adjacent the sample port 30; and the light reflected from the sample passes through the viewing port 32, the wheel 14, and the beam splitter 16 to be directed to both the camera 18 and the sample spectrograph 20. The image produced by the video camera 18 can be viewed to determine whether the sample S is properly positioned within the sample port 30. A reticule (to be described) on the wheel 14 assists in that determination. If the sample is not properly positioned, the sample is repositioned and reevaluated for proper position as many times as is necessary. When the sample is properly positioned, the color is determined using the sample spectrograph 20.

II. Chassis and Enclosure

Figure 1:
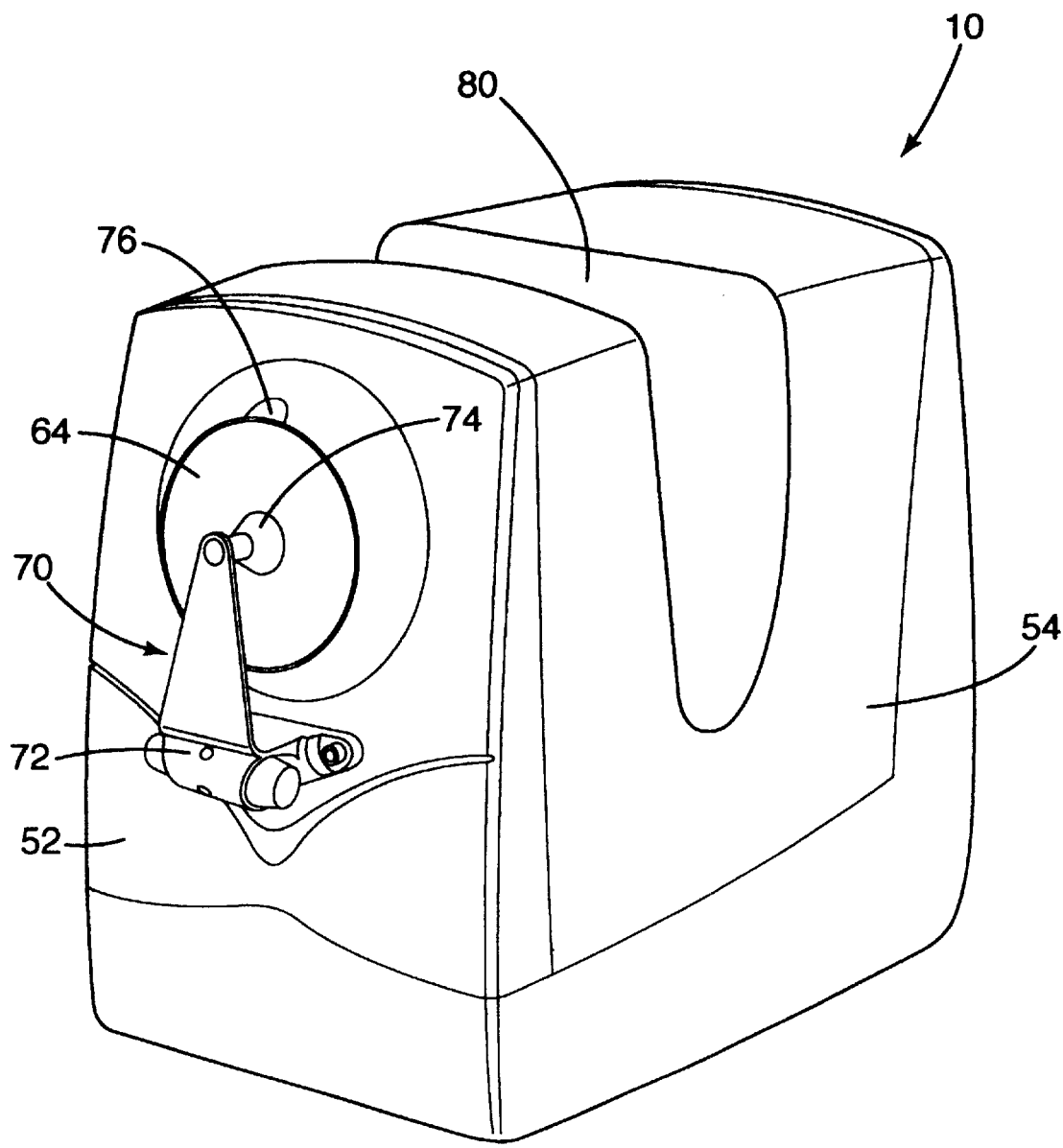
FIG. 1 is a perspective view of the benchtop spectrophotometer with the transmissive sample are cover removed.
Figure 2:
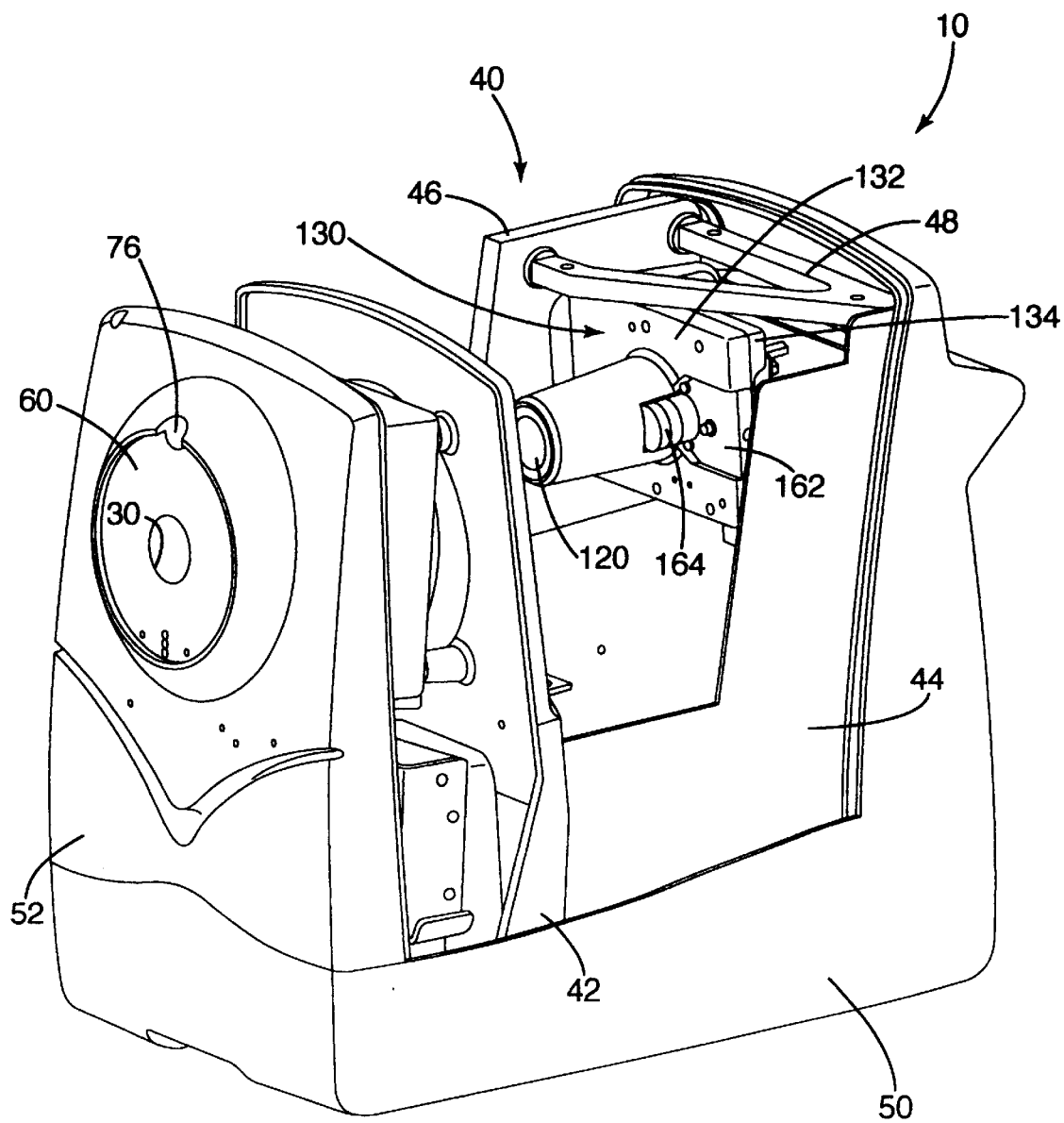
FIG. 2 is a perspective view similar to FIG. 1 with the cover, the enclosure, and the sample holder all removed.

The overall physical construction of the benchtop unit is illustrated in FIGS. 1 and 2. The unit includes a chassis 40 which in turn includes a center casting 42, side castings 44 and 46, a support rib 48, and other components generally known to those skilled in the art. The individual components of the chassis 40 are interconnected to provide a rigid structural framework in which the remaining components are mounted in conventional fashion.

The spectrophotometer (FIGS. 1 and 2) further includes an enclosure base 50, a front casting 52, and an enclosure 54 to protectively enclose the unit 10 in an aesthetically pleasing fashion. The chassis and the enclosure pieces are intersecured in conventional fashion. The front casting 52 defines a plate receiver 60, and the sample port 30 is centered in the plate receiver. A finger access 76 facilitates removal of the sample aperture plates 64 from the plate receiver 60.

III. Measurement and Positioning System

Any one of a plurality of plates 64 may be mounted in the plate receiver 60. Each plate defines a sample aperture 65 (see FIG. 3) of a unique size. In the disclosed embodiment, three plates are provided and have sample aperture diameters of 5.5 mm, 11 mm, and 25 mm, respectively. The aperture 65 in each plate is concentric with, and therefore aligned with, the sample port 30. Each plate has the same outer diameter, so that each plate friction fits within the receiver 60.

The sample holder 70 (FIG. 1) includes a spring-loaded, damped arm 72 and a support 74. The arm 72 biases the support into engagement with the plate 64. The support 74 may be pulled away from the plate 64 either to load a sample or to change the plate 64, for example, to one having a different diameter aperture.

A transmissive sample area 80 permits a transmissive sample (e.g. a fluid) to be positioned between the sphere 12 and the optics 120 for measurement. The inclusion of a transmissive sample area and the associated sample support hardware are well-known to those skilled in the art and therefore will not be described in detail. A cover (not illustrated) also is included to cover the entire transmissive sample opening 80 during use to prevent ambient light from entering the unit during measurement of either a transmissive sample in the area 80 or a reflective sample in the sample holder 70.

As noted above, the integrating sphere 12 (FIG. 3) is generally known to those skilled in the art and most preferably is a six-inch Spectralon integrating sphere manufactured by Labsphere Inc. of North Sutton, N.H. As previously noted, the sphere includes a sample port 30 and a viewing port 32. The sphere further includes an SCI/SCE port 80, a first illuminator 82, and a second illuminator assembly 84. Both of the ports 32 and 80 are oriented 8 degrees from normal to the sample aperture as is customary in d/8 spectrophotometers.

The port 80 includes a removable reflective plug 86 operated by the stepper motor 88 as is conventional in the art. A specular included (SPIN) reading can be taken at port 32 when the plug 86 is in the port 80; and a specular excluded (SPEX) reading can be taken when the plug 86 is withdrawn from the port 80 creating a light trap.

The first illuminator 82 provides illumination for the camera 18 during sample targeting. The illuminator may be a tungsten bulb, a light-emitting diode (LED), or virtually any other illuminator. The first illuminator 82 is actuated only during targeting as will be described. Baffle 112 is included within the sphere 12 to prevent the light from illuminator 82 from shining directly onto the viewing port 32.

The second illuminator assembly 84 is generally well known to those skilled in the art and is operated only during a measurement. The assembly includes a pulse xenon lamp 100, a filter wheel 102, a UV filter wheel 104, and a diffuser 106. The filter wheel includes color balancing and ultraviolet (UV) filters. A stepper motor 108 operates the filter wheel 102. Accordingly, and under computer control, the filtering of the pulse xenon lamp can be controlled by operation of the stepper motor 108.

Baffle 112 prevents the xenon light source from shining directly onto the sample port 30. And the baffle 90 prevents light from the illuminator assembly 84 from shining directly onto the viewing port 32. The construction and placement of the baffles 90 and 112 are known to those skilled in the art.

As previously mentioned, the sample S can be mounted in alignment with the viewing port 30. The sample is mounted against the plate 64 (FIGS. 1 and 3) and over the sample aperture 65.

Turning to the other components in FIG. 3, the beam splitter 16, the camera 18, and the spectrographs 20 and 21 are all individually known in the art. For example, the following components are included in the disclosed instrument. The beam splitter is Product Number 03BSC 005 from Melles Griot. The camera is Product Number AS-02150-000 from Labsphere, Inc. with additional components (e.g. the OVT 511 CMOS camera chip) from OmniVision Technologies, Inc. The spectrographs are Product Number CP20 from Jobin Yvon Horiba. The arrangement, interrelationship, and use of these components is novel in the present invention.

The light L reflected from the sample S and passing through the viewing port 32 also passes through the lens assembly 120 and the reticule/aperture wheel 14 before passing into the beam splitter 16. The beam splitter splits the sample light so that identical light information is directed to both the camera 18 and the sample spectrograph 20. The camera 18 is optically aligned with the viewing port 32 and the sample port 30 by way of a straight path, the beam splitter, and another straight path. The sample spectrograph 20 is optically aligned with the viewing port 32 and the sample port 30 by way of a straight path, the beam splitter, another straight path, and the fiber optic cable 33. Alternatively, the camera 18 could have a straight-line optical alignment with the ports, while the sample spectrograph is aligned with the 90 degree path of the beam splitter 16. Further alternatively, the camera and the sample spectrograph could have separate and independent optical alignments with the ports.

The reference spectrograph 21 is optically connected to a reference port 35 in the sphere by way of the fiber optic cable 37 in conventional fashion for the acquisition of reference information indicative of the output of the illuminator assembly 84 during a color measurement.

IV. Optics Module

Figure 4:
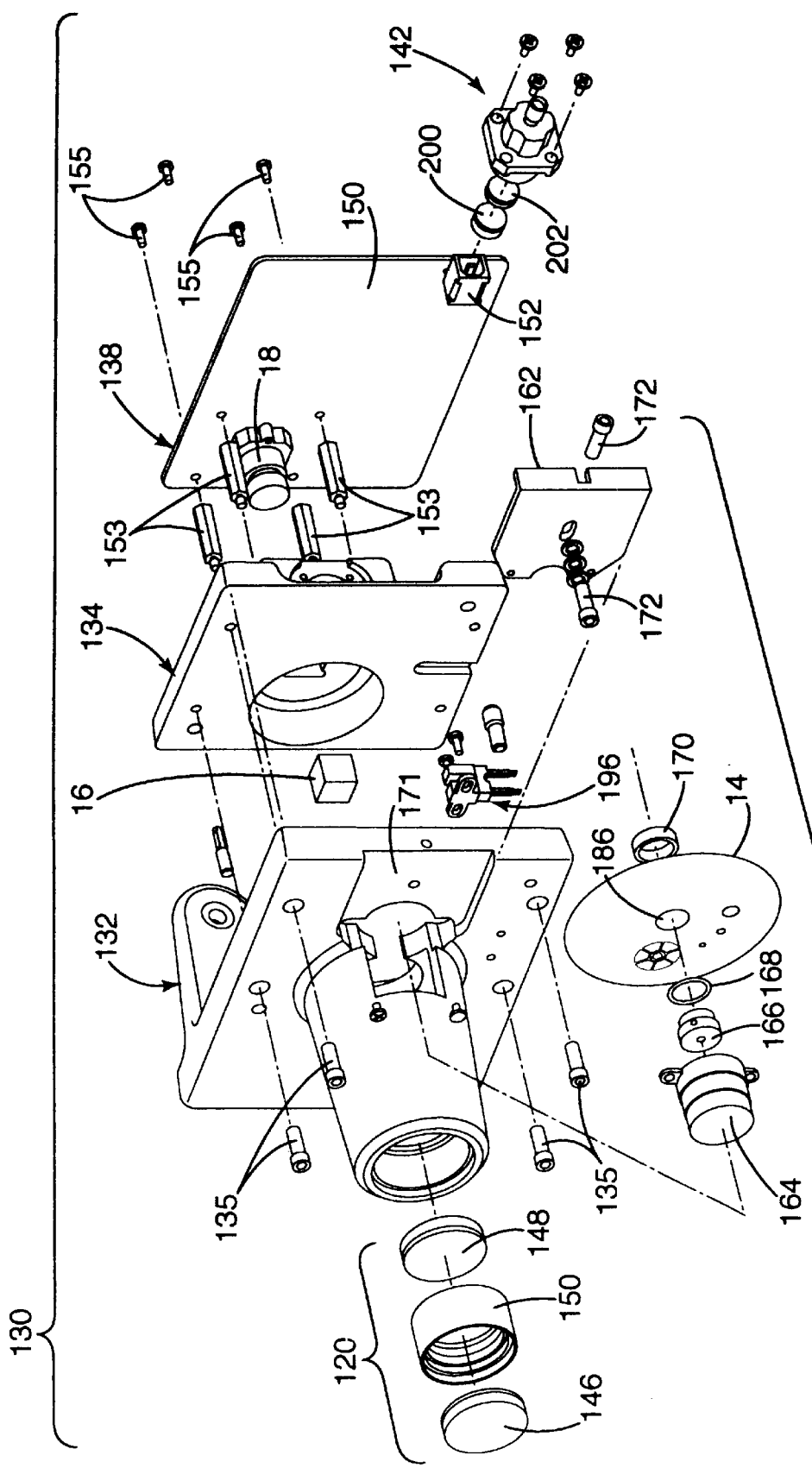
FIG. 4 is a perspective exploded view of the optics module.
Figure 5:
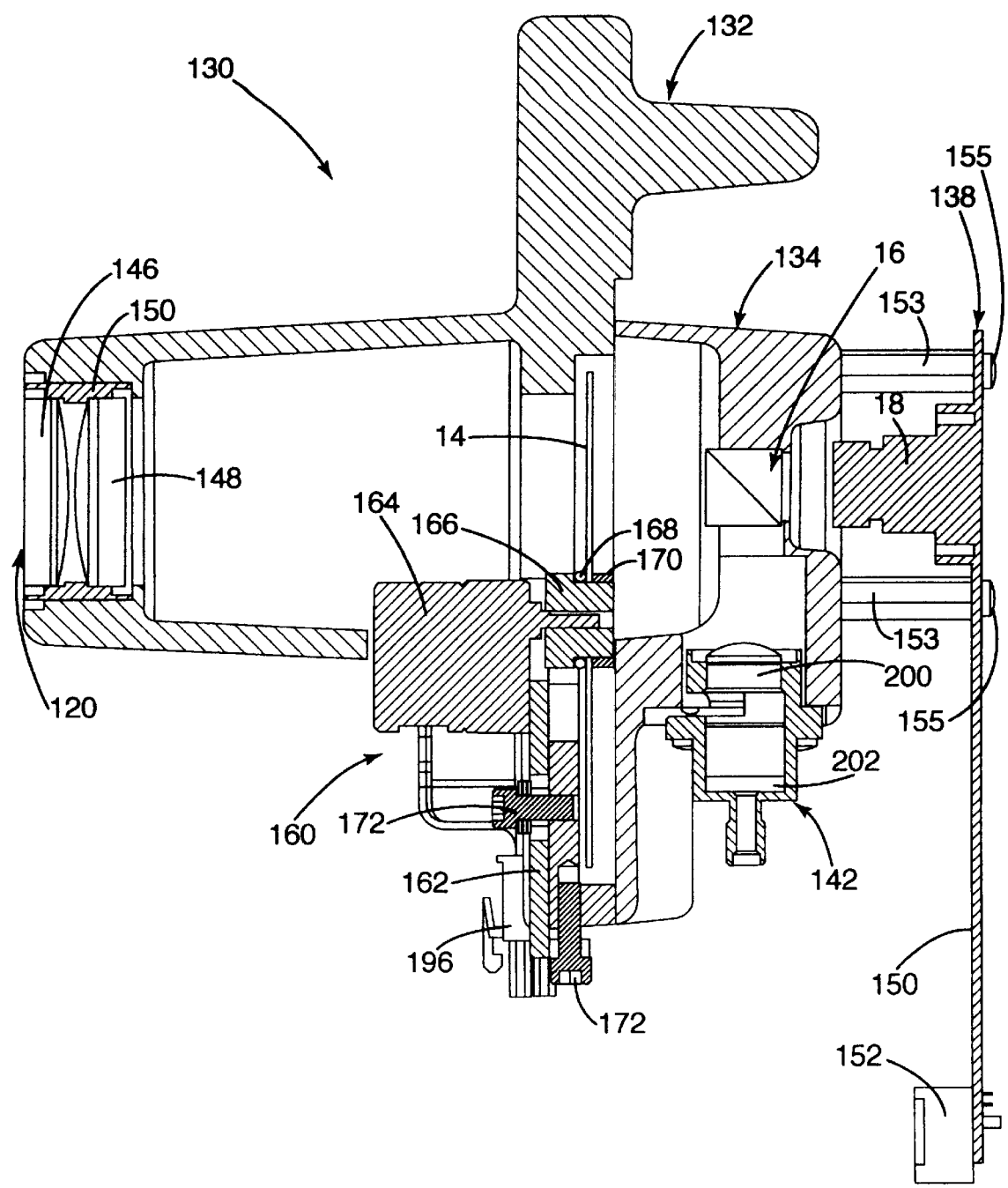
FIG. 5 is a horizontal cross-sectional view through the assembled optics module.

The optics module 130 is visible in FIG. 2 and is illustrated in detail in FIGS. 4 and 5. The optics module includes the lens 120, wheel 14, beam splitter 16, and camera 18 schematically illustrated in FIG. 3. More specifically, the optics module includes a front housing 132, a rear housing 134, the beam splitter 16, a camera assembly 138 (comprising the camera 18), a wheel assembly 140 (including the wheel 14), and a fiber coupling 142. The front and rear housings 132 and 134 are configured to support the remaining components. The two housings are intersecured using shoulder screws 135. The transfer optics assembly 120 includes a pair of achromatic lenses 146 and 148 and a spacer 150. The transfer optics assembly 120 is supported by the front housing 132.

The camera assembly includes a camera card 150 and a camera 18. The card 150 includes a USB connection 152 for plug-and-play connectability with standard operating systems such as Windows. The camera assembly 138 is mounted on the rear housing 134 using spacers 153 and screws 155.

The reticule/aperture wheel assembly 160 (FIGS. 4 and 5) includes the wheel 14, a motor adjust plate 162, and a stepper motor 164. A hub 166, an O-ring 168 and a sleeve 170 are used in mounting the wheel 14 on the stepper motor 164. The stepper motor is in turn mounted to the plate 162 using screws (not shown). The plate 162 is adjustably mounted in the recess 171 on the front housing 132 using the shoulder screws 172. Accordingly, the position of the filter wheel 14 with respect to the optical center of the transfer optics 120 can be precisely optically aligned with the other elements during assembly of the unit.

Figure 6:
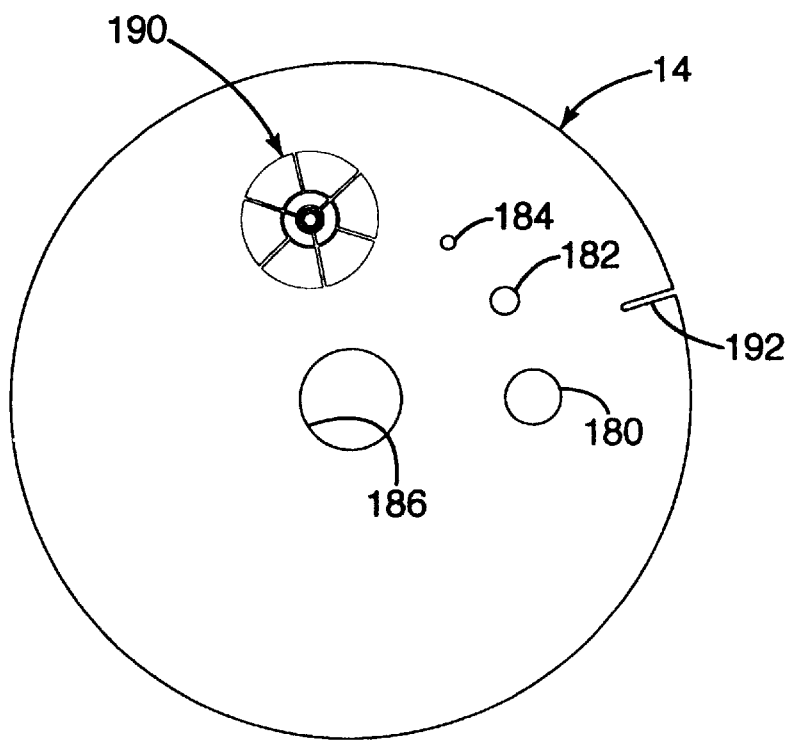
FIG. 6 is a plan view of the reticule/aperture wheel.

The wheel 14 is illustrated in FIG. 6. The wheel defines three sample area apertures 180, 182 and 184 of varying diameters. In the disclosed embodiment, the diameter of aperture 180 is 0.254 inch; the diameter of aperture 182 is 0.109 inch; and the diameter of aperture 184 is 0.056 inch. The wheel aperture sizes are selected in view of the sizes of the sample apertures 65 in the plates 64 so that each of the wheel apertures serves as a field stop for one of the sample apertures. Accordingly, the wheel apertures restrict the target sample area visible to both the camera 18 and the sample spectrograph 20. Preferably, the disk aperture is sized so that the camera and spectrograph see a sample area slightly smaller than the sample aperture 65 so that the plate 64 is not inadvertently included in the image or in the color measurement. The wheel 14 also defines a central mounting aperture 186, which receives the hub 166 (see FIGS. 4 and 5).

Figure 7:
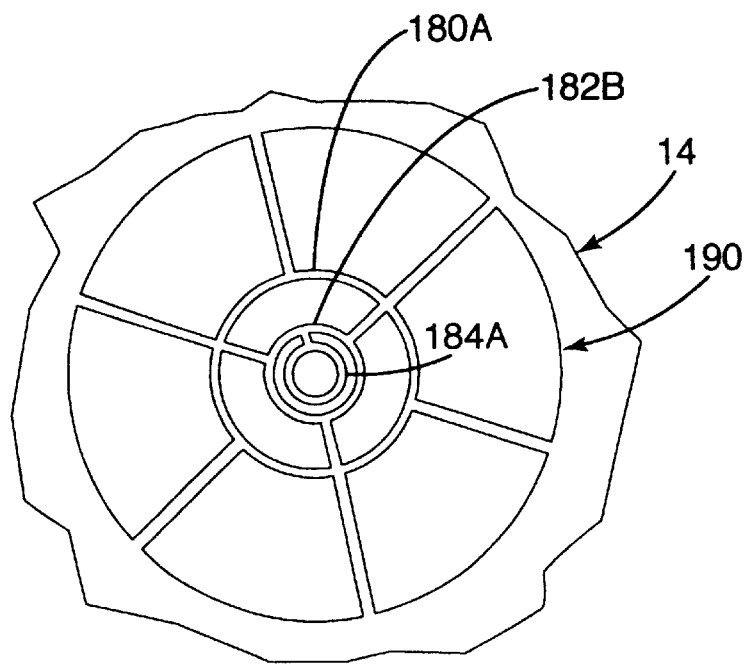
FIG. 7 is an enlarged view of the reticule on the reticule/aperture wheel.

Also, the wheel 14 defines a reticule 190 illustrated in greater detail in FIG. 7. The reticule includes three rings 180a, 182a, and 184a having generally the same diameters as the wheel apertures 180, 182, and 184, respectively. The reticule 190 provides a targeting system for use (a) in aligning the sample within the sample aperture and (b) in evaluating whether the desired portion of the sample is within the selected sample target area.

The centers of each of the apertures 180, 182, and 184 and the reticule 190 are on an imaginary circle concentric with the mounting aperture 186 of the wheel 14. Accordingly, any one of the apertures or reticule can be moved into alignment with the optical path by rotating the wheel 14 about its center. The stepper motor 164 (FIGS. 4 and 5) provides this rotational movement under computer control. The slot 192 in the edge of the wheel 14 provides a mechanism for physically determining the position of the wheel 14 using the optical switch 196 (shown in FIG. 4). As an alternative to a physical device, the reticule could be digitally or otherwise non-physically inserted into the video image.

The fiber optic coupling 142 (FIGS. 4 and 5) includes a focusing lens 200 and a cut-off filter 202. All of these elements are generally well-known to those skilled in the art.

IV. Operation

The present color measurement instrument enables the operator to confirm proper alignment of the sample S with respect to the sample aperture 30.

As the first step in utilizing the unit, the operator selects a desired sample area on a graphic user interface (GUI). In the current embodiment, the GUI is in the controlling software in a computer (not shown) separate from the spectrophotometer 10. The computer and spectrophotometer interface with one another in any manner known to those skilled in the art. The operator also selects an appropriate plate 64 having the desired aperture; and the operator mounts the plate 64 in the plate receiver 60. As noted above, the plate 64 friction-fits within the plate receiver. If a transmissive sample is to be measured, the operator mounts the plate having the largest aperture in the plate receiver; and the operator places the white calibration standard at the sample port.

The operator then selects a sample S to be measured. The sample is either a reflective sample (shown as S) or a transmissive sample (now shown). If the sample is a reflective sample, the operator uses the sample holding mechanism to position the sample against the plate 64. Specifically, the arm 70 is pulled away from the plate 64; the sample is placed against the plate and over the sample aperture 65; and the arm is released so that the sample is pushed against the plate by the support 74. If the sample is transmissive, the operator places the sample into the sample receiving area 80 and more specifically in a conventional sample holding mechanism (not shown). The remainder of this description assumes that a reflective sample is to be measured.

The first illuminator 82 is powered continually except when measurements are taken to provide a light within the sphere 12. The light from the illuminator is diffused or integrated within the sphere. A portion of the light reflects off the sample S through the sample port 30 and the viewing port 32. The reflected light continues through the transfer optics 120 and the reticule wheel 14 to the beam splitter 16. From there, a portion of the light is directed to the camera 18.

The default position of the wheel 14 aligns the reticule with the optical path. Consequently, both the sample S and the reticule 190 are imaged together by the video camera 18. The video image may be displayed on a monitor (not shown) to the operator. In the disclosed embodiment, the image is displayed on the same monitor on which the GUI is displayed. The operator evaluates the position of the sample with respect to the reticule and determines whether the area of interest is properly within the reticule ring 180a, 182a, or 184a corresponding to the selected sample area size. The operator decides whether repositioning the sample is necessary or desirable. The sample is repositioned as necessary or desired until the sample is properly aligned with respect to the reticule 190.

After the sample is properly positioned, the operator indicates through the GUI that a the sample is ready for a color measurement. That indication initiates several steps under computer control. The illuminator 82 is extinguished, and a settling period is initiated during which all light within the sphere is allowed to exit the sphere. Also, the wheel 14 is rotated to align the desired aperture 180, 182, or 184 between the viewing port 32 and the beam splitter 15; and a settling period is initiated during which the wheel settles. The two settling periods may be the same period. After the settling period(s), the second illuminator 100 is actuated and readings are taken by both the sample spectrograph 20 and the reference spectrograph 21. The computer control also operates the plug 86 so that SPIN and/or SPEX readings are taken as selected by the operator using the GUI.

Based on the information acquired by the spectrographs, the unit calculates color information of the sample in accordance with well known techniques. The color information is then displayed to the operator on the GUI and/or is stored in memory, again in accordance with techniques well-known to those skilled in the art.

Accordingly, the present invention provides a system and method for enabling the accurate alignment of the sample for color measurement. The real-time visual confirmation of the sample's location eliminates the guesswork of sample positioning and ensures that the desired portion of the sample is appropriately read. While the color measurement instrument of the present invention has been disclosed in conjunction with an integrating sphere and spectrographs, the invention is applicable to virtually any color measurement instrument using any color measurement technology. Further, while the invention has been described in conjunction with a benchtop instrument, the invention is applicable to portable instruments—and indeed any color measurement instrument.

The above description is that of a preferred embodiment of the invention. Various alterations and changes can be made without departing from the spirit and broader aspects of the invention which are to be interpreted in accordance with the principles of patent law, including the doctrine of equivalents.

The embodiments of the claims in which an exclusive property or privilege is claimed are defined as follows:

1. A color measurement instrument comprising:
   an integrating sphere having a sample port and a viewing port;
   a beam splitter optically aligned with said viewing port and said sample port;
   a camera optically connected to said beam splitter to provide an image of the sample at said sample port; and
   a color measurement system optically connected to said beam splitter to measure the color of the sample at said sample port.

2. A color measurement instrument as defined in claim 1 further comprising reticule means for inserting targeting information into the image of the sample.

3. A color measurement instrument as defined in claim 2 wherein said reticule means comprises a physical reticule optically between said viewing port and said camera.

4. A color measurement instrument as defined in claim 1 further comprising field stop means for providing a selectable field stop optically between said viewing port and said color measurement system.

5. A color measurement instrument as defined in claim 1 wherein said sphere is capable of presenting both specular included and specular excluded output at said viewing port.

6. A color measurement instrument as defined in claim 1 wherein said color measurement system comprises a spectrograph.

7. A color measurement instrument comprising:
   an integrating sphere defining a sample port and a viewing port;
   a camera optically aligned with said sample port and said viewing port for acquiring an image of a sample at said sample port to determine if the sample is properly aligned with said sample port; and
   a color measurement system optically aligned with said sample port and said viewing port to measure the color of the sample at said sample port.

8. A color measurement instrument as defined in claim 7 further comprising a beam splitter having a first output optically connected to said camera and a second output optically connected to said color measurement system.

9. A color measurement instrument as defined in claim 7 further comprising reticule means for inserting reference alignment information into the image of the sample.

10. A color measurement instrument as defined in claim 9 wherein said reticule means comprises a physical reticule optically between said sample port and said camera.

11. A color measurement instrument as defined in claim 7 further comprising field stop means optically between said sample port and said color measurement system for providing a selectable field stop.

12. A color measurement instrument as defined in claim 7 wherein said sphere includes means for enabling specular-included and specular-excluded readings to be taken at said viewing port.

13. A color measurement instrument as defined in claim 7 wherein said color measurement system is a spectrograph.

14. A color measurement instrument comprising:
   an integrating sphere having a sample port and a viewing port, said sphere further including a sample holder for retaining a sample in position at said sample port;
   beam splitter means optically aligned with said viewing port and said sample port for splitting the light reflected thorough said viewing port from a sample at said sample port;
   camera means optically connected to said beam, splitter for acquiring an image of a sample at said sample port;
   a color measurement system optically connected to said beam splitter for determining the color of the sample at said sample port; and
   reticule means for providing sample alignment information to said video camera.

15. A color measurement instrument as defined in claim 14 wherein said beam splitter means comprises a beam splitter.

16. A color measurement instrument as defined in claim 14 wherein said reticule means comprises a physical reticule for optically between said viewing port and said camera means.

17. A color measurement instrument as defined in claim 14 further comprising field stop means optically between said viewing port and said color measurement system for providing a selectable field stop.

18. A color measurement instrument as defined in claim 14 wherein said integrating sphere is capable of providing both specular-included and specular-excluded readings at said viewing port.

19. A color measurement instrument as defined in claim 14 wherein said color measurement system is a spectrograph.

20. A color measurement instrument including:
   an integrating sphere defining a sample port in which a sample may be positioned and a viewing port;
   camera means optically aligned with said ports for capturing an image of the position of the sample within the sample port; and
   measurement means for acquiring information regarding the color of the sample within the sample port, said measurement means optically aligned with said ports.

* * * * *

UNITED STATES PATENT AND TRADEMARK OFFICE
CERTIFICATE OF CORRECTION

PATENT NO. : 6,583,879 B1
DATED : June 24, 2003
INVENTOR(S) : Bernard J. Berg et al.

It is certified that error appears in the above-identified patent and that said Letters Patent is hereby corrected as shown below:

<u>Column 8,</u>
Line 22, after "beam" delete -- , --

Signed and Sealed this

Fourth Day of November, 2003

JAMES E. ROGAN
*Director of the United States Patent and Trademark Office*